United States Patent
Chen (10) Patent No.: US 10,578,865 B2
(45) Date of Patent: Mar. 3, 2020

(54) HEAD-UP DISPLAY APPARATUS, CONTROLLING METHOD THERER, AND VEHICLE

(71) Applicant: BOE TECHNOLOGY GROUP CO., LTD., Beijing (CN)

(72) Inventor: Yanjun Chen, Beijing (CN)

(73) Assignee: BOE TECHNOLOGY GROUP CO., LTD., Beijing (CN)

(*) Notice: Subject to any disclaimer, the term of this patent is extended or adjusted under 35 U.S.C. 154(b) by 0 days.

(21) Appl. No.: 16/114,982

(22) Filed: Aug. 28, 2018

(65) Prior Publication Data
US 2019/0250402 A1     Aug. 15, 2019

(30) Foreign Application Priority Data
Feb. 12, 2018 (CN) .......................... 2018 1 0145816

(51) Int. Cl.
*G09G 5/00* (2006.01)
*G02B 27/01* (2006.01)
(Continued)

(52) U.S. Cl.
CPC ......... *G02B 27/0101* (2013.01); *G02B 27/01* (2013.01); *G03B 21/28* (2013.01);
(Continued)

(58) Field of Classification Search
CPC ............... G02B 27/01; G02B 27/0101; G02B 27/0112; G02B 27/0118; G02B 27/0194;
(Continued)

(56) References Cited

U.S. PATENT DOCUMENTS 5,784,036 A * 7/1998 Higuchi ................. B60K 35/00
345/7
6,932,476 B2 * 8/2005 Sudo .................. G02B 27/2264
353/7
(Continued)

FOREIGN PATENT DOCUMENTS

CN          1830216 A      9/2006
CN        101036606 A      9/2007
(Continued)

OTHER PUBLICATIONS

First Chinese Office Action for Chinese Patent Application No. 201810145816.1, dated Mar. 27, 2019.

*Primary Examiner* — Joe H Cheng
(74) *Attorney, Agent, or Firm* — Kinney & Lange, P.A.

(57) ABSTRACT

The present application relates to a head-up display apparatus, a control method thereof, and a vehicle. The head-up display apparatus comprises: an image projecting device, a display background detecting device, and a processor. The image projecting device is configured to generate an image and project the image onto a preset area on a reflective surface. The display background detecting device is configured to detect optical information of a background space that a user can see through the preset area, wherein the background space and the user are located at opposite sides of the reflective surface. The processor is configured to determine an image displaying mode of the image projecting device based on the optical information, and to control the image projecting device to project images in the determined image displaying mode.

14 Claims, 3 Drawing Sheets

(51) Int. Cl.
  *G03B 21/28* (2006.01)
  *H04N 9/31* (2006.01)
(52) U.S. Cl.
  CPC ......... *H04N 9/31* (2013.01); *B60K 2370/334* (2019.05); *B60K 2370/347* (2019.05)
(58) Field of Classification Search
  CPC . G01J 3/462; G01J 3/50; G03B 21/28; H04N 9/31; B60K 2370/334; B60K 2370/347
  See application file for complete search history.

(56) References Cited

U.S. PATENT DOCUMENTS

| | | | | |
|---|---|---|---|---|
| 7,180,663 | B2* | 2/2007 | Collender | G03B 25/00 359/451 |
| 7,525,734 | B2* | 4/2009 | Aoki | G02B 27/01 359/631 |
| 7,880,130 | B2* | 2/2011 | Sakagami | G01S 7/4814 250/216 |
| 8,013,848 | B2* | 9/2011 | Miyazawa | G03B 21/60 345/204 |
| 8,879,156 | B2* | 11/2014 | Lin | G02B 7/005 359/630 |
| 2006/0203102 | A1 | 9/2006 | Yang et al. | |
| 2008/0043326 | A1* | 2/2008 | Poulsen | G03B 21/60 359/455 |
| 2008/0079753 | A1* | 4/2008 | Victor | G01C 21/365 345/660 |
| 2008/0088646 | A1* | 4/2008 | Sako | G02B 27/0172 345/647 |
| 2009/0110286 | A1* | 4/2009 | Nunn | G06K 9/00818 382/190 |
| 2011/0304611 | A1* | 12/2011 | Suzuki | G06T 15/04 345/419 |
| 2016/0057393 | A1* | 2/2016 | Won | B60R 1/00 348/148 |
| 2016/0112688 | A1* | 4/2016 | Brunn | G06F 3/0485 345/156 |
| 2016/0155269 | A1* | 6/2016 | Cho | G06T 19/006 345/633 |
| 2016/0217590 | A1* | 7/2016 | Mullins | G06T 7/40 |
| 2016/0307346 | A1* | 10/2016 | Staudenmaier | G09G 5/38 |
| 2018/0203227 | A1 | 7/2018 | Xu et al. | |

FOREIGN PATENT DOCUMENTS

| | | | |
|---|---|---|---|
| CN | 104485008 A | 4/2015 | |
| CN | 106101667 A | 11/2016 | |
| CN | 106970748 A | 7/2017 | |
| CN | 206436831 U | 8/2017 | |
| WO | WO-2012034767 A1 * | 3/2012 | ......... G02B 27/0093 |

* cited by examiner

Fig. 1

1 Orange red
2 Orange
3 Orange yellow
4 Yellow
5 Bluish yellow
6 Yellow green
7 Leaf green
8 Green
9 Blue green
10 Blue
11 Ultramarine blue
12 Ultramarine
13 Bluish violet
14 Violet
15 Purplish red
16 Red

HEAD-UP DISPLAY APPARATUS, CONTROLLING METHOD THERER, AND VEHICLE

CROSS-REFERENCE TO RELATED APPLICATION

This application claims priority from Chinese Patent Application No. 201810145816.1 filed on Feb. 12, 2018, the disclosure of which is incorporated herein by reference in its entirety.

BACKGROUND

The present disclosure relates to the field of display technologies, and more particularly, to a head-up display apparatus, a controlling method thereof, and a vehicle.

Head-up display (HUD) technology is useful in vehicle vision assistance. A HUD apparatus can project travel information of a vehicle onto a windshield thereof. The windshield then reflects the travel information so that it can be viewed by the driver of the vehicle. In this way, the driver can obtain travel information without frequently diverting their the line of sight away from road and driving conditions. This capability improves drive and vehicle safety.

Since the content displayed by the HUD apparatus is superposed with the scene in front of the vehicle viewed by the driver through the windshield, it can be difficult for a driver with color-blindness and/or color weakness to accurately identify information displayed in color via the HUD apparatus due to their deficiency in color recognition, which may result in misjudgment of information and even danger.

SUMMARY

According to a first aspect of embodiments of the present disclosure, there is proposed a head-up display apparatus comprising: an image projecting device configured to generate and project an image to be displayed, and to project the image onto a preset area on a reflective surface; a display background detecting device configured to detect optical information of a background space that a user can see through the preset, wherein the background space and the user are located at opposite sides of the reflective surface; and a processor configured to determine an image displaying mode of the image projecting device based on the optical information, and to control the image projecting device to project images in the determined image displaying mode.

In some embodiments, the optical information comprises at least one of luminance information or color information, and parameters of the image displaying mode include at least one of image color or image luminance.

In some embodiments, the head-up display apparatus further comprises a color recognition ability device configured to obtain color recognition ability information of the user. The processor is further configured to determine the image displaying mode of the image projecting device based on the obtained color recognition ability information of the user and the optical information.

In some embodiments, the color recognition ability device comprises a color vision analyzer configured to perform a color recognition ability test on the user to obtain a color vision analysis result for the user. The color recognition ability device is further configured to obtain the color vision analysis results by the color vision analyzer, and to utilize the color vision analysis result as the color recognition ability information.

In some embodiments, the color recognition ability device further comprises: an identity identifying device configured to identify identity information of the user; a memory configured to store the color vision analysis result for the user in association with the identity information. The color recognition ability device is further configured to: obtain the identity information of the user by the identity identifying device; obtain the color vision analysis result for the user from the memory based on the identity information; and utilize the color vision analysis result as the color recognition ability information.

In some embodiments, the identity identifying device is further configured to: collect biometric information of the user, the biometric information including at least one of face information, fingerprint information, or iris information; and identify the identity information of the user based on the biometric information.

In some embodiments, the display background detecting device is implemented as one or more of a camera, a photosensor, and other electronic device having an image information collecting function.

In some embodiments, the processor is further configured to: provide a plurality of candidate image displaying modes based on the optical information: and apply the image displaying mode selected by the user from the plurality of candidate image displaying modes to the image projecting device.

According to a second aspect of embodiments of the present disclosure, there is proposed a method of controlling a head-up display apparatus. The head-up display apparatus comprises an image projecting device configured to generate and project an image to be displayed, and to project the image onto a preset area on a reflective surface. The method comprises steps of: detecting optical information of a background space that a user can see through the preset area, the background space and the user are located at opposite sides of the reflective surface; determining an image displaying mode of the image projecting device based on the optical information; and controlling the image projecting device to project images in the determined image displaying mode.

In some embodiments, the optical information comprises at least one of luminance information or color information, and parameters of the image displaying mode include at least one of image color or image luminance.

In some embodiments, the method further comprises the step of obtaining color recognition ability information of the user. The step of determining the image displaying mode of the image projecting device based on the optical information comprises: determining the image displaying mode of the image projecting device based on the obtained color recognition ability information of the user and the optical information.

In some embodiments, the step of obtaining the color recognition ability information of the user further comprises: performing a color recognition ability test on the user to obtain a color vision analysis result for the user; and utilizing the color vision analysis result as the color recognition ability information.

In some embodiments, the step of obtaining the color recognition ability information of the user further comprises: identifying identity information of the user; obtaining the color vision analysis result for the user from a color vision analysis result memory based on the identity information; and utilizing the color vision analysis result as the color recognition ability information.

In some embodiments, the step of identifying the identity information of the user further comprises: collecting biometric information of the user; and identifying the identity information of the user based on the biometric information. The biometric information includes at least one of face information, fingerprint information, or iris information.

In some embodiments, the step of determining the image displaying mode of the image projecting device based on the optical information comprises: providing a plurality of candidate image displaying modes; and applying the image displaying mode selected by the user from the plurality of candidate image displaying modes to the image projecting device.

According to a third aspect of embodiments of the present disclosure, there is proposed a vehicle comprising a head-up display apparatus according to any of the above embodiments.

It should be noted that the above general description and the following detailed description are intended to be exemplary and illustrative but not to limit the present disclosure.

BRIEF DESCRIPTION OF THE DRAWINGS

The drawings herein are incorporated into the specification and form a part of the specification. The drawings illustrate embodiments in consistent with the present disclosure and serve to explain the principles of the present disclosure together with the specification.

DETAILED DESCRIPTION

Exemplary embodiments will be described in detail herein, examples of which are illustrated in the accompanying drawings. When the following description relates to the accompanying drawings, the same or similar reference numbers in different figures denote the same or similar elements, unless otherwise indicated. Implementations described in the following exemplary embodiments do not represent all embodiments consistent with the present disclosure. Instead, they are merely examples of the apparatus and method consistent with aspects of the present disclosure as detailed in the following claims.

Figure 1:
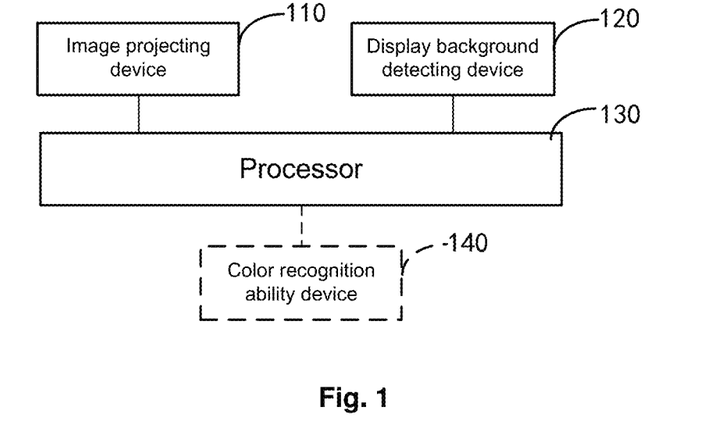
FIG. 1 is a block diagram of a head-up display apparatus according to an exemplary embodiment of the present disclosure.

FIG. 1 is a block diagram of a head-up display apparatus according to an exemplary embodiment of the present disclosure. The head-up display apparatus can be applied to a vehicle such as a car, an airplane, a ship, or the like. The present disclosure takes the scene in which a user (i.e., a driver) drives a car as an example for description.

As shown in FIG. 1, the head-up display apparatus comprises an image projecting device 110, a display background detecting device 120, and a processor 130.

The image projecting device 110 is configured to generate and project an image to be displayed. Specifically, the image projecting device projects the image onto a preset area on a reflective surface.

In some embodiments, the reflective surface (or projection surface) may be the windshield of a vehicle or a portion thereof. The image may include travel information, such as a navigation route, a traveling speed, and the like, which is not limited in this embodiment.

It should be noted that, in this embodiment, the projection position can be set in front of the windshield, which means that a projected image is formed in front of the vehicle. As such, it appears to the user that, the projected image is located in front of the vehicle when it is viewed by the user after being reflected by the reflective surface, so that the user can conveniently view the actual environment in front of the vehicle and the driving information without changing focus of eyes of the user.

The display background detecting device 120 is configured to detect optical information of the background space that the user can see through the preset area, the background space and the user are located at opposite sides of the reflective surface.

When the user views the projected image, he/she will see the actual environment in front at the same time. The so-called "the background space that the user can see through the preset area" refers to the environmental zones in front of the vehicle entering the line of sight of the user at the same time when the user views the projected image.

In some embodiments, the optical information includes at least one of luminance information or color information.

The display background detecting device 120 can be implemented as one or more of a camera, a photosensor, or a further electronic device having an image information collecting function.

In some embodiments, the display background detecting device 120 can be implemented as an ambient luminance sensor disposed in front of the windshield to obtain ambient luminance information of the background space. The ambient luminance sensor is used to sense the real-time luminance of the environment, and sensing parameters may be adjusted according to the projection distance and projection position of the projected image.

In some embodiments, the display background detecting device 120 can be implemented as an ambient color detecting module for detecting ambient color information of the background space. The ambient color detecting module (e.g., a camera or other electronic device having an image capturing function) can be disposed at a rear-view mirror so as to obtain the color information of the background space.

Figure 2:
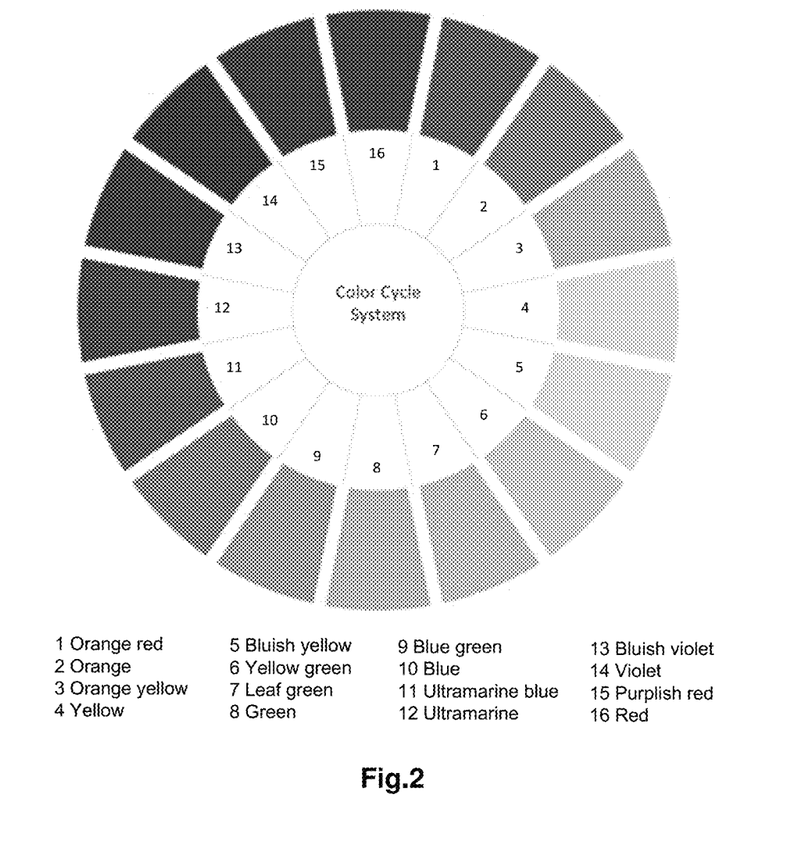
FIG. 2 is a schematic diagram of a color cycle system according to an exemplary embodiment of the present disclosure.

It should be noted that the ambient color detecting module is configured to detect colors of a plurality of positions in the background space. When the colors of the plurality of positions are the same or similar to each other (within an angle of 45° in the color cycle system shown in FIG. 2), it is considered that the ambient colors detected by the ambient color detecting module are the same. In practical applications, it can be regarded that the same environment has one ambient color, and different environments with large differences in color have different ambient colors. For example, if the background space includes any one of a sky, a desert, a forest, and a road, there is only one ambient color. And if the background space includes a number (n) of the sky, the desert, the forest, and the road, there are n ambient colors.

The processor 130 is configured to determine an image displaying mode of the image projecting device 110 based on the optical information, and to control the image projecting device 110 to project in the determined image displaying mode. It should be understood that the processor 130 may be any of various general-purpose or special-purpose processing units, chips or circuits, and it may be a vehicle electronic system or a part thereof or be separate from the vehicle electronic system.

In some embodiments, parameters of the image displaying mode include at least one of the image color or the image luminance.

In some embodiments, the processor 130 is configured to determine the ambient color and the ambient luminance level of the background space based on the optical information, and to adjust the image projecting device 110 based thereon. For example, when the luminance level of the background space is high, the processor 130 can increase the luminance of the image projected by the image projecting device 110, making it easier for the user to view the projected image. For another example, when the color of the background space is mainly yellow (for example, a desert scene), the processor 130 may replace the yellow color in the image projected by the image projecting device 110 with a color that is more easily distinguished from the background color, thereby avoiding the situation where the displayed image is unrecognizable due to its same color as the that of the environment. In this way, the current user can clearly see the displayed information of the HUD, reducing the probability of a traffic accident caused by information identification errors.

It can be seen from the above description that, in the present embodiment, the display background detecting device 120 is configured to obtain the ambient luminance information and the ambient color information of the background space, and the processor 130 is configured to determine the projected image displaying mode for the current user, to control the image projecting device to project images based on the determined image displaying mode, and to adjust the color settings and contrast of the projected images in real time with reference to the environmental information, so as to avoid traffic accidents caused by information identification errors and reduce driving risks.

In some embodiments, the head-up display apparatus of FIG. 1 may also comprise a color recognition ability device 140. The color recognition ability device 140 is configured to obtain the information on the color recognition ability of the user.

In some embodiments, the processor 130 is further configured to determine the image displaying mode of the image projecting device 110 based on the color recognition ability information of the user determined by the color recognition ability device 140 and the optical information.

In some embodiments, the color recognition ability device 140 may comprise a color vision analyzer, which is configured to perform a color recognition ability test on the user to obtain a color vision analysis result for the user. The color vision analysis result may include color blindness type and color sensitivity of the current user, and the like.

The color recognition ability device 140 provides the obtained color vision analysis result to the processor 130 as the color recognition ability information.

The color recognition ability device 140 may also comprise a memory for storing the color vision analysis results of the user.

In another embodiment, the color recognition ability device 140 also includes an identity identifying device, which is configured to identify the identity information of the user.

In some embodiments, the identity information uniquely corresponds to the current user, and examples of which may be, for example, ID number, fingerprint information, iris information, face information, and the like. The identity identifying device can be disposed in the vehicle. For example, a face (iris) recognizing device is suspended directly in front of the user's position in the head of the vehicle to obtain the face (iris) information of the current user. For another example, a fingerprint recognizing device is disposed at a location where it is convenient for the user to contact, for example, on the steering wheel and the like, so as to obtain the fingerprint information of the current user.

In this embodiment, the memory may be configured to store the color vision analysis result for the user in association with the identity information. Specifically, after obtaining the color vision analysis result for the user, the color vision analysis result may be stored based on the identity information of the user. That is, the corresponding relationship between the identity information and the color vision analysis result for the user is established, and saved locally in the head-up display apparatus. Alternatively, the corresponding relationship may also be uploaded to the server for subsequent queries.

The color recognition ability device 140 may look up the memory according to the identity information, and provide the found color vision analysis result corresponding to the identity information to the processor 130 as the color recognition ability information.

The color recognition ability information may by default be obtained directly via a color vision analysis at first. Alternatively, the color recognition ability information may by default be obtained by looking up the memory based on the identity information at first, and the color vision analyzer is only activated when the corresponding data cannot be found in the memory.

In some embodiments, if the color vision analysis result cannot be found according to the identity information of the current user, a prompt message for prompting the user to conduct the standard color blindness test may be output, so as to test the color recognition ability and the color sensitivity of the user, thereby obtaining the color vision analysis result.

It should be noted that the form and content of the standard color vision analysis can be found in the related art, which is not limited in this embodiment.

In some embodiments, the processor 130 may determine whether the current user is a person with deficiency in color recognition according to the identity information of the user or the color vision analysis result. If yes, the processor 130 may determine a personalized projected image displaying mode according to the color blindness type (for example, red-green color blindness, yellow-blue color blindness, etc.) and the color vision sensitivity (complete color weakness, red color weakness, green color weakness, blue-yellow color weakness, etc.) of the current user; otherwise, it determines to employ the normal projected image displaying mode.

In some embodiments, a plurality of personalized projected image displaying modes may be preset according to different color blindness types and different color sensitivities, so that after determining the identity information of the current user, the color blindness type and the color sensitivity of the user may be determined, and then the projected image displaying mode for the current user is determined according to the color blindness type and the color sensitivity.

As an example, for the current user who is a person with red-green color blindness, meaning that the current user cannot distinguish between red and green, if the traffic light at the current intersection is red, the user may not be alerted. Therefore, a personalized projected image displaying scheme can be set for the current user, for example, the red color of the traffic light can be corrected to a color which is recognizable for the user (such as blue), and the contrast of the corrected color may be increased.

It should be noted that, neither the specific division of various color blindness types and color sensitivities nor the specific color correcting scheme corresponding to each color blindness type and color sensitivity is limited in this embodiment.

It can be seen from the above description that, in the present embodiment, the identity information of the current user may be identified by the identity identifying device, or the color vision analysis result may be obtained by the color vision analyzer directly, and then a customized projected image displaying scheme may be proposed according to the color vision analysis result, which can provide a favorable displaying of images for a specific population.

In another embodiment, the processor 130 is further configured to:

provide a plurality of candidate image displaying modes based on the optical information;

apply the image displaying mode selected by the user from the plurality of candidate image displaying modes to the image projecting device.

In some embodiments, the processor 130 may output a plurality of candidate image displaying modes for the current user to select according to his/her own preferences, and to determine a color scheme, contrast parameters, and the like. For example, for a person with red-green color blindness, red color may be corrected to blue color or purple color, and the contrast of the respective color may be set.

In this approach, it is able to determine the projected image displaying mode in combination with the user's preferences, to improve the personalization level of the head-up display apparatus, and thus to improve the user experience.

Figure 3:
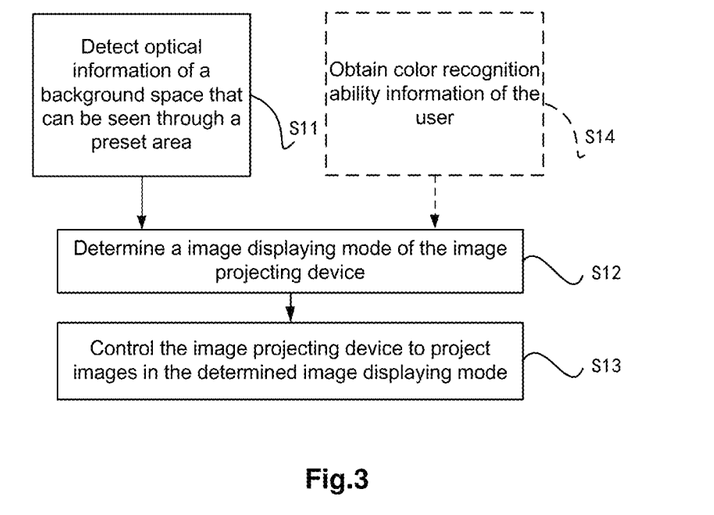
FIG. 3 is a flowchart of a head-up display method according to an exemplary embodiment of the present disclosure.

FIG. 3 is a flowchart of a method for controlling a head-up display apparatus according to an exemplary embodiment of the present disclosure. The method can be applied to a vehicle such as a car, an airplane, a ship, or the like. The head-up display apparatus performing the method comprises an image projecting device configured to generate and project an image to be displayed. Specifically, the image projecting device projects the image onto a preset area on a reflective surface. The head-up display apparatus may be the head-up display apparatus shown in FIG. 1, and thus the description made above in connection with FIG. 1 is likewise applicable here, and details thereof will not be described herein again.

As shown in FIG. 3, the method includes the following steps S11-S13:

S11: Detecting optical information of the background space that a user can see through the preset area, the background space and the user are located at opposite sides of the reflective surface.

In some embodiments, the optical information includes at least one of luminance information or color information.

S12: Determine an image displaying mode of the image projecting device according to the optical information.

In some embodiments, parameters of the image displaying mode include at least one of the image color or the image luminance.

In some embodiments, the step S12 further includes: providing a plurality of candidate image displaying modes; and applying the image displaying mode selected by the user from the plurality of candidate image displaying modes to the image projecting device.

S13: Controlling the image projecting device to project in the determined image displaying mode.

In some embodiments, the method further includes the step S14 of obtaining color recognition ability information of the user. At this time, the step of determining the image displaying mode of the image projecting device includes, determining the image displaying mode of the image projecting device according to the obtained color recognition ability information of the user and the optical information.

In some embodiments, the step S14 further includes: performing a color recognition ability test on the user to obtain a color vision analysis result for the user; and utilizing the color vision analysis result as the color recognition ability information.

In another embodiment, the step S14 further includes: identifying identity information of the user; obtaining the color vision analysis result for the user from a color vision analysis result memory based on the identity information; and utilizing the color vision analysis result as the color recognition ability information.

In some embodiments, the step of identifying the identity information of the user further includes: collecting biometric information of the user, which includes at least one of face information, fingerprint information, or iris information; and identifying the identity information of the user based on the biometric information.

In another aspect, the present disclosure also provides a vehicle that can include a head-up display apparatus (e.g., a head-up display apparatus in FIG. 1) in accordance with the above embodiments.

In some embodiments, the vehicle may include any one of a car, a train, an airplane, and a ship.

The present disclosure is described below in conjunction with the specific embodiments, which are set forth to illustrate and explain but not to limit the disclosure. The features of the embodiments and the embodiments themselves described in the present disclosure may be combined with each other under the condition of no conflict.

Figure 4A:
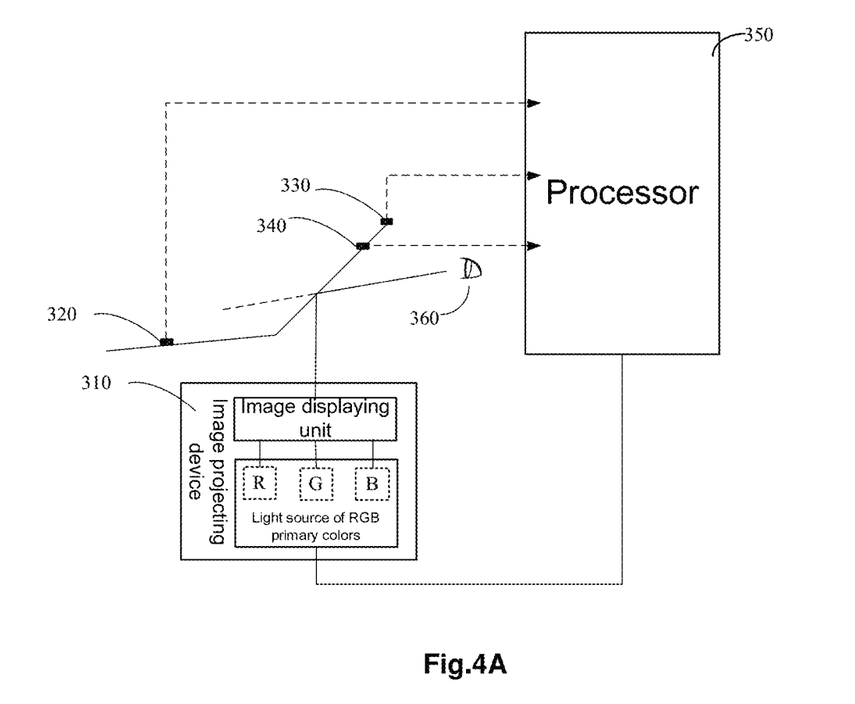
FIG. 4A is a block diagram of a head-up display apparatus according to another exemplary embodiment of the present disclosure.
Figure 4B:
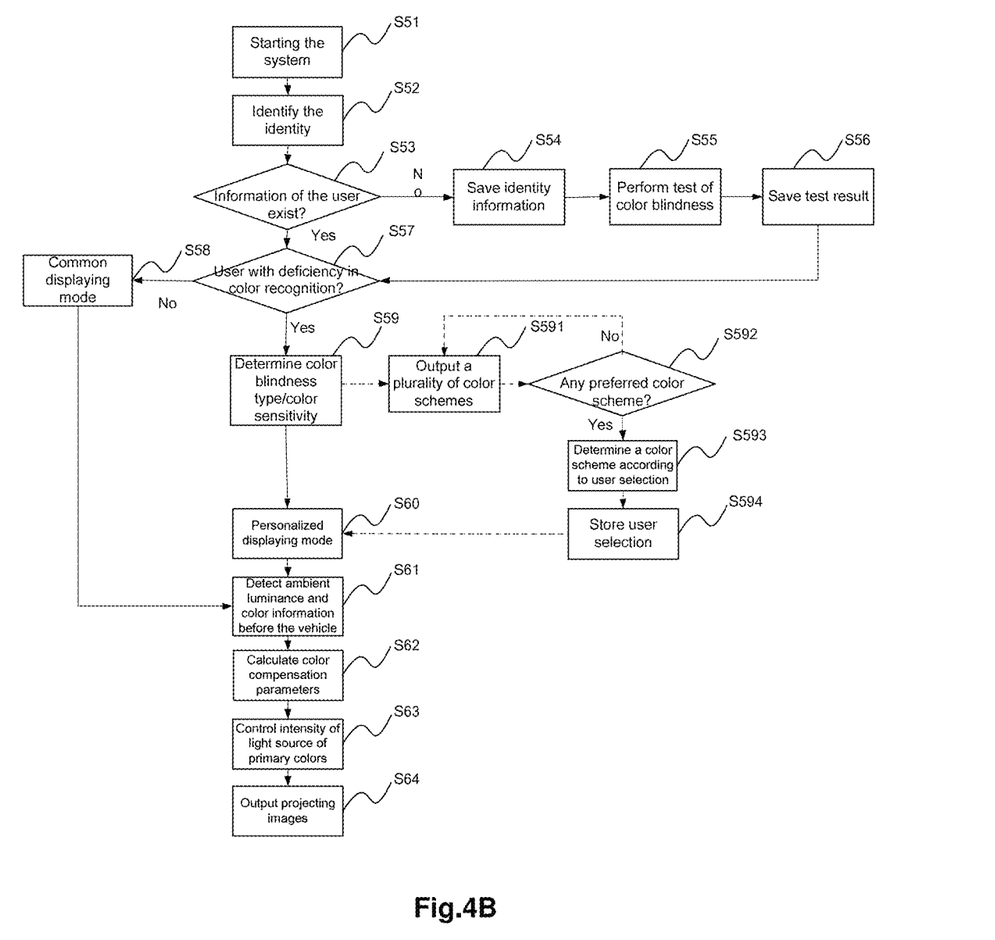
FIG. 4B is a flowchart of a head-up display method according to another exemplary embodiment of the present disclosure.

FIG. 4A is a block diagram of a specific head-up display apparatus according to an exemplary embodiment of the present disclosure, and FIG. 4B is a flowchart of a head-up display method according to an exemplary embodiment of the present disclosure. As shown in FIG. 4A, the apparatus comprises an image projecting device 310 based on a light source of RGB primary colors, an ambient luminance sensor 320, an image capturing device 330, an identity identifying device 340, and a processor 350. The combination of the ambient luminance sensor 320 and the image capturing device 330 corresponds to the display background detecting device 120 in FIG. 1, and the identity identifying device 340 corresponds to the color recognition ability device 140 in FIG. 1.

The processor 350 may obtain ambient luminance information, ambient color information, and identity information by receiving signals from the ambient luminance sensor 320, the image capturing device 330, and the identity identifying device 340, respectively, and obtain a corresponding color vision analysis result according to the identity information. Thereby, the processor 350 can determine how to adjust the displaying mode of the image projecting device 310 and achieve an instant and personalized setting by adjustment.

As shown in FIG. 4A, the ambient luminance sensor 320 can be disposed in front of the windshield for sensing the real-time luminance of the environment, and the specific sensing parameters can be adjusted according to the projection distance and projection position of the projected image.

The image capturing device 330 can be disposed close to the center rear view mirror for acquiring the color and pattern of the zones in front of the vehicle. The image capturing device 330 may be, for example, a simple single camera or other electronic device with a camera, which is not limited in this embodiment.

The identity identifying device 340 (e.g., fingerprint/iris/face identifying device) may be disposed at different positions of the vehicle according to the identification principle. For example, the face/iris identifying device may be suspended directly in front of the user's (360) position in the head of the vehicle, and the fingerprint recognition device may be disposed on the steering wheel for facilitating the user 360 to contact.

As shown in FIG. 4B, the method comprises the following steps:

S51: Receiving a control instruction for starting a head-up display apparatus triggered by a user;

S52: An identity identifying device performs user identification based on fingerprint/face/iris information and the like;

S53: Querying whether there is identity information of the user; if yes, skipping to step S57; if not, proceeding to step S54;

S54: Prompting the user to collect the identity information (such as fingerprint/iris/face information), and storing the collected identity information;

S55: Performing a standard color blindness test on the user to test his/her color recognition ability and color sensitivity;

S56: Storing the test result based on the identity information of the user;

S57: Determining whether the user is a person with deficiency in color recognition; if not, proceeding to step S58; if yes, executing step S59;

S58: Displaying a projected image in a normal displaying mode;

S59: Determining a color blindness type/color sensitivity of the user;

S60: Determining a personalized displaying mode according to the color blindness type/color sensitivity of the user;

S61: Detecting the ambient luminance and color information of zones in front of the vehicle;

S62: Calculating compensation parameters for the RGB primary colors of each pixel in the projected image based on the color blindness type and the color sensitivity, the ambient luminance, and the ambient color of the zones in front of the vehicle;

S63: Controlling the intensity of each of the RGB primary colors at each pixel based on the color compensation parameter;

S64: Outputting the projected image being color-corrected.

Further, in view of the fact that a person with deficiency in color recognition or an ordinary user may have a higher sensitivity to some colors, a faster reaction speed, or a personal preference for some colors, the user can also select a color scheme in this embodiment. Specifically, before the step S60 of determining a personalized displaying mode according to the color sensitivity of the user, the method may further comprise the following steps S591-S593 of:

S591: Outputting a plurality of color schemes for the user to select according to the color sensitivity of the user;

S592: Determining whether there is a color scheme preferred by the user among the provided color scheme; if not, repeating step S591; if yes, executing step S592:

S592: Determine a personalized displaying mode for the user according to the selection of the user;

S593: Storing the color scheme selected by the user this time.

In comparison with the related art, the head-up display apparatus, the head-up display method and the vehicle proposed by embodiments of the present disclosure can identify user's identity by iris, fingerprint or face identifying device, perform a color recognition ability test on the user, and apply a personalized color display scheme to a user with deficiency in color recognition. The present disclosure can performs a real-time color correction on the output screen by adjusting the intensity of a light source of RGB primary colors in conjunction with the ambient luminance, the foreground color and the color recognition ability of the user on the basis of the personalized color display scheme, which may effectively mitigate or even avoid the observation obstacle or confusion of the user. As such, a user with deficiency in color recognition can also accurately identify HUD information, thereby avoiding traffic accidents caused by information identification errors and reducing driving risks Other embodiments of the present disclosure will be readily apparent to those skilled in the art, after considering the specification and practicing the disclosure disclosed herein. The present disclosure is intended to cover any variation, use, or adaptive modification of the present disclosure, which are in accordance with the general principle of the present disclosure and which include common knowledge or commonly used means in the art that have not been disclosed in the present disclosure. The specification and embodiments are merely illustrative, and the actual scope and spirit of the invention is limited by the following claims.

It should be understood that the present disclosure is not limited to the precise structure described above and shown in the drawings, and various modifications and changes may be made without departing from the scope thereof. The scope of the disclosure is only limited by the following claims.

The invention claimed is:

1. A head-up display apparatus, comprising:
   an image projecting device configured to generate and project an image to be displayed, wherein the image projecting device projects the image onto a preset area on a reflective surface;
   a display background detecting device configured to detect optical information of a background space that a user can see through the preset area, wherein the background space and the user are located at opposite sides of the reflective surface;
   a color recognition ability device configured to obtain color recognition ability information of the user; and
   a processor configured to determine an image displaying mode of the image projecting device based on the obtained color recognition ability information of the user and the optical information, and to control the image projecting device to project images in the determined image displaying mode,
   wherein the color recognition ability device comprises:
      a color vision analyzer configured to perform a color recognition ability test on the user to obtain a color vision analysis result for the user,
      wherein the color recognition ability device is further configured to:
      obtain the color vision analysis results by the color vision analyzer, and
      utilize the color vision analysis result as the color recognition ability information.

2. The apparatus of claim 1, wherein the optical information comprises at least one of luminance information or color information, and parameters of the image displaying mode include at least one of image color or image luminance.

3. The apparatus of claim 1, wherein the color recognition ability device further comprises:
an identity identifying device configured to identify identity information of the user;
a memory configured to store the color vision analysis result for the user in association with the identity information,
wherein the color recognition ability device is further configured to:
obtain the identity information of the user by the identity identifying device,
obtain the color vision analysis result for the user from the memory based on the identity information; and
utilize the color vision analysis result as the color recognition ability information.

4. The apparatus of claim 3, wherein the identity identifying device is further configured to:
collect biometric information of the user, the biometric information including at least one of face information, fingerprint information, or iris information; and
identify the identity information of the user based on the biometric information.

5. The apparatus of claim 1, wherein the display background detecting device is implemented as one or more of a camera, a photosensor, and other electronic device having an image information collecting function.

6. The apparatus of claim 1 wherein the processor is further configured to:
provide a plurality of candidate image displaying modes based on the optical information:
apply the image displaying mode selected by the user from the plurality of candidate image displaying modes to the image projecting device.

7. A method of controlling a head-up display apparatus comprising an image projecting device configured to generate and project an image to be displayed, wherein the image projecting device projects the image onto a preset area on a reflective surface, the method comprising:
detecting optical information of a background space that a user can see through the preset area, wherein the background space and the user are located at opposite sides of the reflective surface;
obtaining color recognition ability information of the user;
determining an image displaying mode of the image projecting device based on the obtained color recognition ability information of the user and the optical information; and
controlling the image projecting device to project images in the determined image displaying mode,
wherein the step of obtaining the color recognition ability information of the user further comprises:
performing a color recognition ability test on the user to obtain a color vision analysis result for the user,
utilizing the color vision analysis result as the color recognition ability information.

8. The method of claim 7, wherein the optical information comprises at least one of luminance information or color information, and
parameters of the image displaying mode include at least one of image color or image luminance.

9. The method of claim 7, wherein the step of obtaining the color recognition ability information of the user further comprises:
identifying identity information of the user;
obtaining the color vision analysis result for the user from a color vision analysis result memory based on the identity information; and
utilizing the color vision analysis result as the color recognition ability information.

10. The method of claim 9, the step of identifying the identity information of the user further comprises:
collecting biometric information of the user, wherein the biometric information includes at least one of face information, fingerprint information, or iris information;
identifying the identity information of the user based on the biometric information.

11. The method of claim 7, the step of determining the image displaying mode of the image projecting device based on the optical information comprises:
providing a plurality of candidate image displaying modes;
applying the image displaying mode selected by the user from the plurality of candidate image displaying modes to the image projecting device.

12. A vehicle comprising a head-up display apparatus of claim 1.

13. The vehicle of claim 12, wherein the optical information comprises at least one of luminance information or color information, and
parameters of the image displaying mode include at least one of image color or image luminance.

14. The vehicle of claim 12, wherein the color recognition ability device further comprises:
an identity identifying device configured to identify identity information of the user;
a memory configured to store the color vision analysis result for the user in association with the identity information,
wherein the color recognition ability device is further configured to:
obtain the identity information of the user by the identity identifying device,
obtain the color vision analysis result for the user from the memory based on the identity information; and
utilize the color vision analysis result as the color recognition ability information.

* * * * *

UNITED STATES PATENT AND TRADEMARK OFFICE
CERTIFICATE OF CORRECTION

PATENT NO. : 10,578,865 B2
APPLICATION NO. : 16/114982
DATED : March 3, 2020
INVENTOR(S) : Chen

Page 1 of 1

It is certified that error appears in the above-identified patent and that said Letters Patent is hereby corrected as shown below:

On the Title Page

Item [54], and in the Specification Column 1 Line 2:
Delete "THERER"
Insert --THEREFOR--

Signed and Sealed this
Sixteenth Day of June, 2020

Andrei Iancu
*Director of the United States Patent and Trademark Office*